United States Patent [19]

Cushman

[11] Patent Number: 4,943,151
[45] Date of Patent: Jul. 24, 1990

[54] SCHEINER-PRINCIPLE VERNIER OPTOMETER

[75] Inventor: William B. Cushman, Pensacola, Fla.

[73] Assignee: The United States of America as represented by the Secretary of the Navy, Washington, D.C.

[21] Appl. No.: 370,521

[22] Filed: Jun. 23, 1989

[51] Int. Cl.⁵ ............................ A61B 3/10; A61B 3/02
[52] U.S. Cl. .................................... 351/203; 351/232; 351/243; 351/237; 351/211
[58] Field of Search ............... 351/203, 237, 239, 243, 351/246, 232, 234, 214, 215, 211

[56] References Cited

U.S. PATENT DOCUMENTS

| | | | |
|---|---|---|---|
| 3,634,003 | 1/1972 | Guyton . | |
| 4,408,846 | 10/1986 | Balliet | 351/203 |
| 4,618,231 | 10/1986 | Genco et al. | 351/237 |
| 4,778,268 | 10/1988 | Randle | 351/203 |

Primary Examiner—Rodney B. Bovernick
Attorney, Agent, or Firm—Thomas E. McDonnell; George Jameson

[57] ABSTRACT

In a preferred embodiment, the optometer apparatus includes: a pinhole aperture plate having first and second horizontally positioned apertures disposed on opposite sides of a first optical axis; first and second orthogonally-oriented polarizing filters respectively covering the first and second horizontally positioned apertures; a positive lens having an optical axis on the first optical axis and being positioned at a distance of approximately one focal length from the pinhole aperture plate; a lens system having an optical axis on the first optical axis; a slit aperture plate having a vertical slit and being disposed on the first optical axis and between the positive lens and the lens system; third and fourth vertically positioned polarizing filters selectively disposed adjacent to the slit aperture plate to divide the slit vertically, the third and fourth polarizing filters being respectively oriented parallel to the first and second polarizing filters; a monochromatic light source for propagating light along the first optical axis through the lens system, through portions of the third and fourth polarizing filters covering the slit, through the positive lens and through the first and second apertures to form first and second images on the retina of a person's eye; and movable means attached to the slit aperture plate, the lens system and the monochromatic light source for moving the slit aperture plate, the lens system and the monochromatic light source together in a fixed relationship along the first optical axis to enable the person to align the first and second images.

20 Claims, 1 Drawing Sheet

U.S. Patent   Jul. 24, 1990   4,943,151
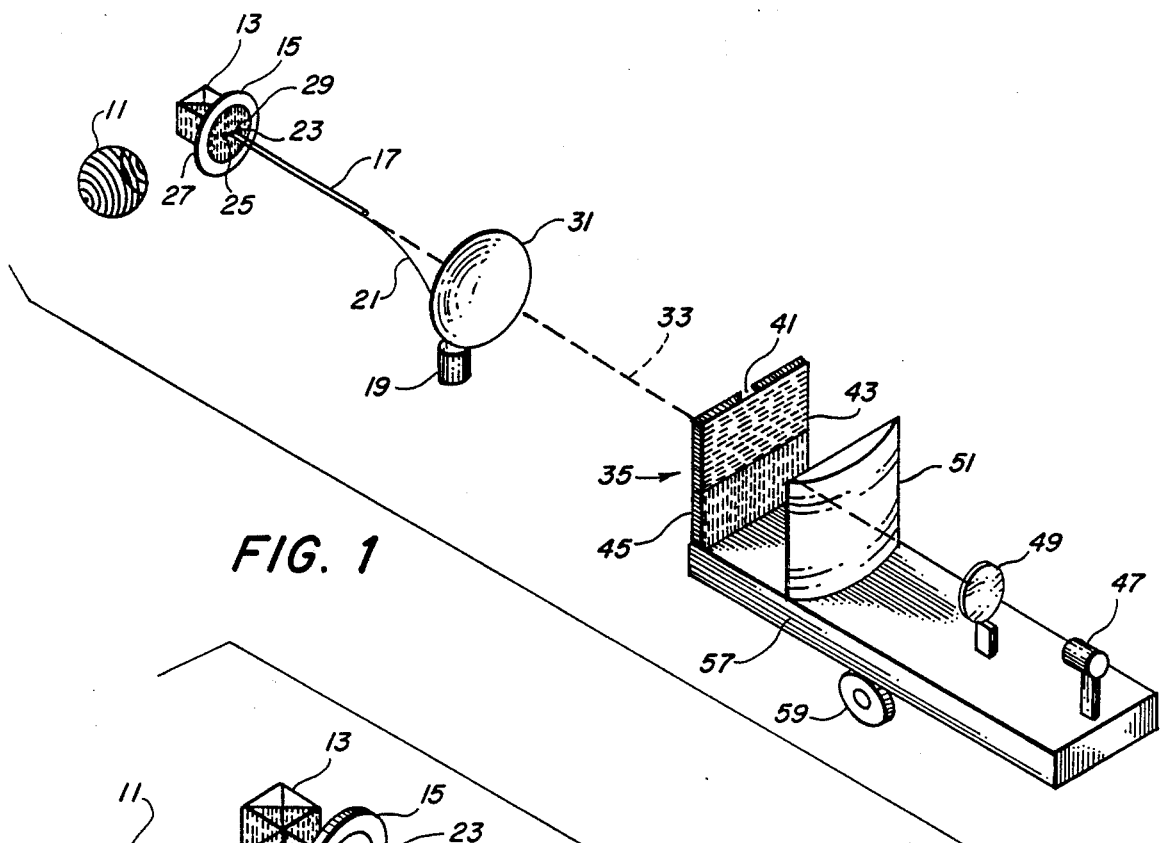
FIG. 1
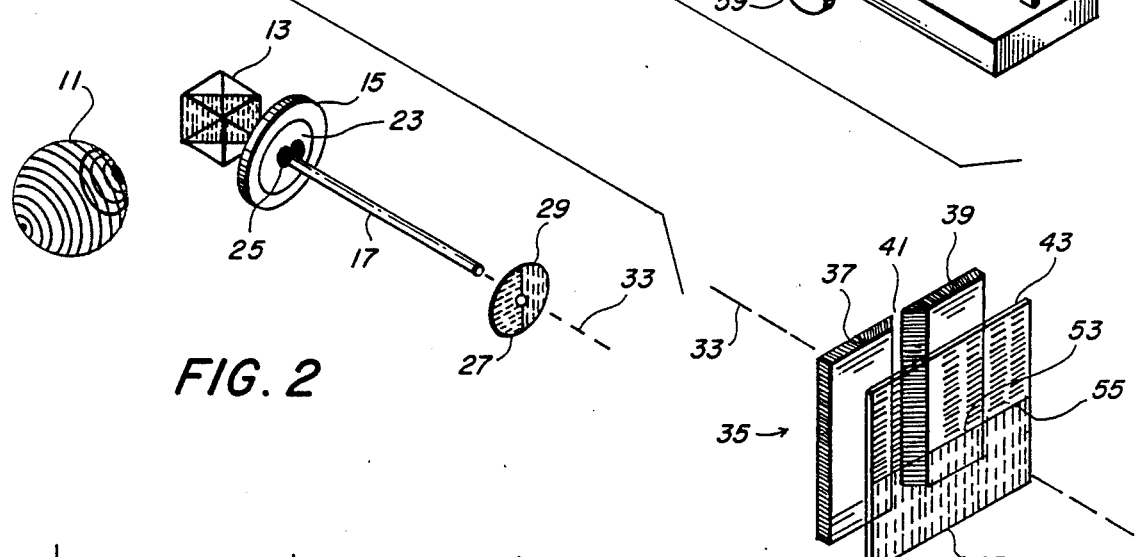
FIG. 2
FIG. 3
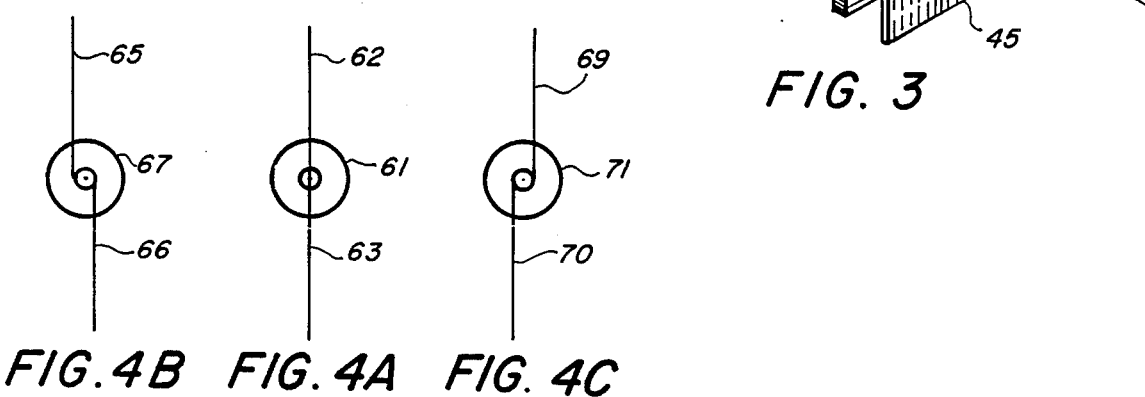
FIG. 4B   FIG. 4A   FIG. 4C

SCHEINER-PRINCIPLE VERNIER OPTOMETER

BACKGROUND OF THE INVENTION

1. Field of the Invention

The present invention relates to optometers and particularly to a Scheiner-principle vernier optometer apparatus, and method therefor, for measuring, e.g., the resting state of accomodation of a person in a darkened environment.

2. Description of the Prior Art

The need for precise lens accommodation to bring visual targets into sharp focus on the retina is far more urgent at night, when contrast is very low, than in bright daylight. But it is at precisely this time that many individuals become myopic and further reduce the quality of an already poor visual image. In many professions this phenomenon, sometimes called the "dark focus of accommodation", is of little consequence. But for some, for example pilots flying at night, it can mean the difference between life and death. A reliable screening apparatus capable of measuring the refractive state of individuals in the dark could, therefore, provide useful preventive information. Either the Laser-Badal optometer or the common vernier optometer could be used in this way, but both of them have problems as they are usually implemented.

Currently, much research in the area of "dark focus" has relied on the Laser-Badal optometer. This device is simple and produces accurate results. It is, however, quite difficult to use in practice, and some individuals are completely unable to produce data with this device. In addition, data taken from a Laser-Badal optometer is typically corrected for the chromaticity of the light source, usually a Helium-Neon laser with an output wavelength of 632.8 nm (nano meters), by adding 0.33 D (diopters) of myopia. This correction presumes to match the experimental result to one that would have resulted if the light source were at a wavelength of 585 nm (yellow light). A more direct approach is to use a 585 nm light source. However, laser light sources at this wavelength are not readily available.

An alternative optometer is the vernier optometer, which is based on the Scheiner principle and uses polaroids and a vernier task. A vernier optometer is simple to construct and to use. However, even a fairly sophisticated vernier optometer does not reliably produce accurate results.

The problems associated with prior art vernier optometers appear to occur for two reasons. First, prior art vernier optometers make no attempt to maintain the optical axis of the subject's eye in tight alignment with the optical axis of the vernier optometer. However, alignment of the subject's eye with the vernier image must be precisely controlled or readings will be discrepant. This phenomenon can be easily demonstrated by looking through an ordinary Scheiner-principle vernier optometer and intentionally moving the instrument or the eye in a direction perpendicular to the vernier image. The relationship of the vernier lines will also change. Second, the data taken from a vernier optometer are sensitive to the chromatic content of the light source used and/or any chromatic aberrations present in lenses or produced by small apertures. More particularly, a Scheiner-principle optometer requires a fair amount of light to get a usable image through the small Scheiner apertures, and a white light source is an easy way to get enough light through those small apertures. However, white light is, by definition, a collection of many different wavelengths, all of which are refracted to varying degrees by the human eye. These differences in refraction amount to about 0.8 diopters when comparing red and blue light sources in an optometer. So the problem in such Scheiner-principle vernier optometers is, if the light source is white, exactly which wavelength in the white light should be used as the criterion. Furthermore, in a vernier optometer based on the Scheiner-principle that uses a broad-band white light source, chromatic aberrations from the optometer lenses and pinhole apertures may be appreciable. These aberrations can become a serious source of error since the human lens is also known to exhibit appreciable chromatic aberrations.

OBJECTS OF THE INVENTION

Accordingly, it is an object of this invention to provide an improved optometer apparatus and method therefor.

Another object of this invention is to measure the dark focus of accommodation under low ambient light levels.

Another object of this invention is to measure the resting state of accommodation of a person in a darkened environment.

Another object of this invention is to provide a Scheiner-principle vernier optometer apparatus, and method therefor, for measuring the dark focus of accommodation of a person.

A further object of this invention is to provide a Scheiner-principle vernier optometer which is capable of maintaining the optical axis of a person's eye in tight alignment with the optical axis of the optometer during the measurement of the person's dark focus of accommodation.

SUMMARY OF THE INVENTION

These and other objects of this invention are achieved by a method and optometer apparatus that includes: a pinhole aperture plate having first and second horizontally positioned apertures disposed on opposite sides of a first optical axis; first and second orthogonally-oriented polarizing filters respectively covering said first and second horizontally positioned apertures; a positive lens having an optical axis on said first optical axis and being positioned at a distance of approximately one focal length from said pinhole aperture plate; a lens system having an optical axis on said first optical axis; a slit aperture plate having a vertical slit and being disposed on said first optical axis and between said positive lens and said lens system; third and fourth vertically positioned polarizing filters selectively disposed adjacent to said slit aperture plate to divide said slit vertically, said third and fourth polarizing filters being respectively oriented parallel to said first and second filters; a monochromatic light source for propagating light along said first optical axis through said lens system, through portions of said third and fourth filters covering said slit, through said positive lens and through said first and second apertures to form first and second images on the retina of a person's eye; and movable means attached to said slit aperture plate, said lens system and said monochromatic light source for moving said slit aperture plate, said lens system and said monochromatic light source together in a fixed relationship along said first optical axis to enable the person to align the first and second images.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views, and wherein:

FIG. 1 illustrates a diagram of a preferred embodiment of the invention, showing the essential elements of the invention and their interrelationships with respect to each other;

FIG. 2 is an exploded perspective view of the viewing end of the embodiment of FIG. 1;

FIG. 3 is an exploded perspective view of the slit aperture stop plate and polarizing filters contained in the embodiment of FIG. 1; and FIGS. 4A, 4B and 4C are depictions of views that could be seen by a subject or person as he adjusts the apparatus of the embodiment of FIG. 1.

DETAILED DESCRIPTION OF THE PREFERRED EMBODIMENT

Before proceeding with the Detailed Description, the terms "optometer", "Scheiner-principle optometer" and "dark focus of accomodation" are defined below to aid in the reader's understanding of the present invention.

Optometer—Any one of several objective or subjective devices for measuring the refractive state of the eye. (Synonym: opsiometer, optimeter, refractometer)

Scheiner-principle optometer—An optometer employing, as an operating principle, multiple pupillary apertures to produce a corresponding multiplicity of images when the image viewed is not in focus.

Dark focus of accommation—A phenomenon, generally recognized as the "resting state" of the eye in the absence of sufficient stimulation to activate focusing mechanisms. This situation usually occurs in the dark and, thus, it is called the "dark focus of accommodation". This "resting state" in the dark is typically myopic, so a synonym for the phenomenon is "night myopia". A related phenomenon occurs when light is being received by the eye but there is no detail (as, for example, when flying in a cloud). This related phenomenon is called "empty field myopia".

Referring now to FIG. 1, a preferred embodiment of the optometer apparatus of the invention is shown. The apparatus of FIG. 1 measures the accommodative state of a subject or person (not shown) by the act of adjusting to vernier alignment two lighted bars in accordance with the teaching of the invention.

FIG. 1 shows the subject's eye 11 looking into a cube-type beam splitter 13 which is adjacent to a pinhole aperture stop plate 15, with a hollow tube 17 affixed to the center of and penetrating the pinhole aperture stop plate 15. The hollow tube 17 is internally illuminated by red light from a red light emitting diode 19 by way of a fiber optic filament 21. The pinhole aperture stop plate 15 also contains two pinhole (or Scheiner) apertures 23 and 25 located horizontally equidistant from the hollow tube 17 with a distance between centers of approximately 3 millimeters.

Lying adjacent to the pinhole aperture stop plate 15 on the side opposite from the cube-type beam splitter 13 are two polarizing filters 27 and 29 which cover the pinhole apertures 23 and 25. The polarizing filters 27 and 29 are oriented 90 degrees with respect to each other, with, for example, the polarizing filter 27 being oriented horizontally and the polarizing filter 29 being oriented vertically. A positive Badal lens 31 is disposed on the optical axis 33 of the hollow tube 17 at a distance of approximately one focal length from the pinhole aperture stop plate 15 and exactly one focal length from a slit aperture stop plate 35 which is also on the optical axis 33. The slit aperture stop plate 35 is comprised of two exemplary rectangularly-shaped metallic plates 37 and 39 (FIG. 3) horizontally displaced from each other by a distance of, for example, 10 to 20 thousandth of an inch in order to form a vertical slit 41 therebetween. As will become apparent later, the distance between the Badal lens 31 and the slit 41 in the slit aperture stop plate 35 defines the zero point of the optometer apparatus of FIG. 1 as a whole.

Adjacent to the slit aperture stop plate 35 are two contiguous polarizing filters 43 and 45 that are oriented such that light passed through the filter 43 and the top half of the slit 41 becomes polarized parallel to the orientation of the polarizing filter 27 (adjacent to the pinhole aperture stop plate 15), while light passed through the filter 45 and the bottom half of the slit 41 becomes polarized parallel to the orientation of the polarizing filter 29 (also adjacent to the pinhole aperture stop plate 15). In other words, light emerging from the slit 41 in the slit aperture stop plate 35 is directed by the polarizing filters 27 and 29 such that light from the top half of the slit 41 emerges from only the pinhole aperture 25 in the pinhole aperture stop plate 15, while light from the bottom half of the slit 41 emerges from only the pinhole aperture 23 in the pinhole aperture stop plate 15. It should be understood that the terms "from only the pinhole aperture 25" and "from only the pinhole aperture 23" refer to the maximum extinction possible with the respective polarizing filters 27 and 29.

Yellow light from a yellow light emitting diode 47 propagates through a converging lens 49, a cylinder lens 51 and the polarizing filters 43 and 45 to illuminate the slit aperture stop plate 35. The positions of the converging lens 49 and cylinder lens 51 are adjusted so that the image or yellow light from the yellow light emitting diode 47 is spread vertically within the slit 41 of the slit aperture stop plate 35 after passing through the polarizing filters 43 and 45. The position of the slit aperture stop plate 35, adjacent edges 53 and 55 (FIG. 3) of the polarizing filters 43 and 45 at the intersection with the slit 41 (in the slit aperture stop plate 35), the optical axis of the converging lens 49, the optical axis of the cylinder lens 51 and the axis of the yellow light emitting diode 47 all lie on the optical axis 33 of the hollow tube 17. Furthermore, the slit aperture stop plate 35, polarizing filters 43 and 45, cylinder lens 51, converging lens 49 and yellow light emitting diode 47 are all rigidly affixed to a movable carriage 57. The movable carriage 57 may be translated or moved along a path parallel to the optical axis 33 of the hollow tube 17 by means of a rack and pinion gear 59 which may be operated by the subject.

FIG. 2 shows an exploded perspective view of a front portion of the optometer apparatus of FIG. 1. More specifically, FIG. 2 shows the subject's eye 11, the cube-type beam splitter 13, the pinhole aperture stop plate 15 and its pinhole apertures 23 and 25, the hollow tube 17 and the polarizing filters 27 and 29 somewhat enlarged, with the elements 13, 15, 17, 27, and 29 translated along the optical axis 33 of the hollow tube 17 to better illustrate their relative positioning.

FIG. 3 shows an exploded perspective view of the slit aperture stop plate 35 and polarizing filters 43 and 45 somewhat enlarged and translated along the optical axis 33 of the hollow tube 17 to better illustrate their relative positioning.

In the operation of the optometer apparatus of FIG. 1, the image of the slit 41 in the slit aperture stop plate 35 is projected through the pinhole apertures 23 and 25 in the pinhole aperture stop plate 15 as two bundles or rays of light. These bundles of light are separated laterally by the separation of the pinhole apertures 23 and 25 in the pinhole aperture stop plate 15. One of these bundles of light is from the top half of the slit 41 in the slit aperture stop plate 35 and the other bundle of light is from the bottom half of the slit 41 in the slit aperture stop plate 35. This division into two discrete bundles of light is accomplished by the orientations of the various polarizing filters 27, 29, 43 and 45. If the distance from the slit aperture stop plate 35 is one focal length from the Badal lens 31, then the light exiting the pinhole apertures 23 and 25 in the pinhole aperture stop plate 15 will be collimated. That is, it will be at optical infinity from the perspective of the subject.

If the subject's eye 11 is focused at optical infinity while viewing the image so produced, the subject will see something similar to the image depicted in FIG. 4A, where 61 is a red "bull's eye" 61 produced by internal reflections within the hollow tube 17, 62 is the image of, for example, the top half of the slit 41 in the slit aperture stop plate 35, and 63 is the image of the bottom half of the slit 41 in the slit aperture stop plate 35. In this case the displacement in the two bundles of light 62 and 63 exiting the pinhole aperture stop plate 15 is compensated for by the optics of the eye 11 to bring them into vernier alignment on the retina (not shown) of the eye 11.

If the subject's eye is focused beyond optical infinity (he is hyperopic), then the bundles of light exiting the pinhole apertures 23 and 25 of the pinhole aperture stop plate 15 are deviated less in their path to the retina of the subject's eye 11, and the subject will see an image similar to the image depicted in FIG. 4B. In the image shown in FIG. 4B, 65 is the image from the top half of the slit 41 in the slit aperture stop plate 35, 66 is the image from the bottom half of the slit 41 in the slit aperture stop plate 35, and 67 represents the red "bull's eye" in this example.

On the other hand, if the subject's eye 11 is focused closer than optical infinity (he is myopic), then the bundles of light exiting the pinhole apertures 23 and 25 of the pinhole aperture stop plate 15 are deviated more in their path to the retina of the subject's eye 11, and the subject will see an image similar to the image depicted in FIG. 4C. In the image shown in FIG. 4C, 69 is the image from the top half of the slit 41 in the slit aperture stop plate 35, 70 is the image from the bottom half of the slit aperture stop plate 35, and 70 represents the red "bull's eye" in this example.

The position of the movable carriage 57 and it's attached elements (35, 43, 45, 51, 49, and 47) can be translated or moved by the subject along the optical axis 33 of the hollow tube 17. Such a translation brings the illuminated slit 41 of the slit aperture stop plate 35 closer to or further from the Badal lens 31.

If the carriage 57 is translated toward the Badal lens 31, then the two light bundles respectively exiting the pinhole apertures 23 and 25 of the pinhole aperture stop plate 15 are caused to deviate, or spread, relative to one another. If the optics of the subject's eye are myopic (that is, causing too much convergence of the two light bundles to produce vernier alignment of the image of the slit 41 of the slit aperture stop plate 35 on the retina of the subject's eye 11), then a divergence of the light bundles exiting the pinhole apertures 23 and 25 would tend to compensate for the excess convergence due to myopia and bring the image into vernier alignment. Conversely, a translation of the carriage 57 away from the Badal lens 31 will cause the two light bundles exiting the pinhole apertures 23 and 25 to diverge and, thus, to compensate for a hyperopic subject. This relationship between convergence and divergence of the two light bundles exiting the pinhole apertures 23 and 25 of the pinhole aperture stop plate 15 and the image of the slit 41 of the aperture stop plate 35 on the subject's retina is exploited by the present invention as discussed below.

The subject translates or moves the carriage 57 to a point where the two halves of the image from the slit 41 of the slit aperture stop plate 35 are in vernier alignment. The deviation from one focal length between the Badal lens 31 and the slit 41 in the slit aperture stop plate 35 is then a direct function of the deviation of the optics of the subject's eye 11 from optical infinity. Deviations of the carriage 57 toward the Badal lens 31 reflect a myopic condition and deviations away from the Badal lens 31 reflect a hyperopic condition.

Translations of the carriage 57 by a subject can be measured electronically and displayed digitally by means apparent to anyone skilled in the art. If the Badal lens 31 has a power of 10 diopters, the focal length of the Badal lens 31 is 10 centimeters. A translation of the carriage 57 toward or away from one focal length distance to the Badal lens 31 represents a deviation from optical infinity of the subject's eye 11 of one diopter for every centimeter of translation. The exact relationship between the power of the Badal lens 31, the slit 41 in the slit aperture stop plate 35, and the subject's dioptric deviation from infinity is given by the equation:

$$S_d = B^2 M - B$$

where $S_d$ is the subject's dioptric deviation in diopters, B is the power of the Badal lens 31 in diopters, and M is the distance between the Badal lens 31 and the slit 41 in meters. Solving the equation gives the lens power required to correct the subject's eye 11 to infinity. That is, negative numbers indicate myopia, and positive numbers indicate hyperopia.

Timed presentation of stimuli are sometimes desirable in an experimental setting to prevent the subject from "attending" too closely to the optometer apparatus being used rather than to an object at a distance dictated by the experiment. In more conventional designs, stimulus timing has been accomplished with the use of mechanical shutters and electronic timers. The present invention has an additional advantage in that a large portion of the light from the yellow light-emitting diode 47 is actually presented to the subject's eye 11, thus reducing the light output required to achieve a particular luminance. Light emitting diodes turn on and off very quickly compared to incandescent sources, and may be switched electronically with ease. Such a timed presentation can be utilized in the present invention by electronic means apparent to anyone of ordinary skill in the art.

Therefore, what has been described is a Scheiner-principle vernier optometer for measuring the resting state of accommodation in a darkened environment.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by letters patent of the United States is:

1. An optometer apparatus comprising:
   a pinhole aperture plate having first and second horizontally positioned apertures disposed on opposite sides of a first optical axis;
   first and second orthogonally oriented polarizing filters respectively covering said first and second horizontally positioned apertures;
   a positive lens having an optical axis on said first optical axis and being positioned at a distance of approximately one focal length from said pinhole plate;
   a slit aperture plate having a vertical slit;
   third and fourth vertically positioned polarizing filters selectively disposed adjacent to said slit aperture plate to divide said slit vertically, said third and fourth polarizing filters being respectively oriented parallel to said first and second polarizing filters;
   a cylinder lens; and
   a monochromatic light source for emitting light at a first wavelength;
   said slit aperture, said third and fourth polarizing filters, said cylinder lens and said monochromatic light source being fixedly positioned relative to one another by translatable along the optical axis of said positive lens.

2. The optometer apparatus of claim 1 wherein said pinhole aperture plate further includes a third aperture located between said first and second horizontally positioned apertures, said optometer apparatus further including:
   an elongated hollow tube disposed in said aperture; and
   a second monochromatic light source for internally illuminating said elongated hollow tube with light at a second wavelength.

3. The optometer apparatus of claim 1 further including:
   beam-splitting means for allowing superposed viewing of the optometer image over any other image.

4. The optometer apparatus of claim 1 further including:
   a converging lens to focus the light from said monochromatic light source to said pinhole aperture plate.

5. The optometer apparatus of claim 1 wherein:
   said positive lens is a Badel lens.

6. An optometer apparatus comprising:
   a pinhole aperture plate having first and second horizontally positioned apertures disposed on opposite sides of a first optical axis;
   first and second orthogonally oriented polarizing filters respectively covering said first and second horizontally positioned apertures;
   a positive lens having an optical axis on said first optical axis and being positioned at a distance of approximately one focal length from said pinhole aperture plate;
   a lens system having an optical axis on said first optical axis;
   a slit aperture plate having a vertical slit and being disposed on said first optical axis and between said positive lens and said lens system;
   third and fourth vertically positioned polarizing filters selectively disposed adjacent to said slit aperature plate to divide said slit vertically, said third and fourth polarizing filters being respectively oriented parrallel to said first and second filters;
   a monochromatic light source for propagating a light image along said first optical axis through said lens system, through portions of said third and fourth filters covering said slit, through said positive lens and through said first and second apertures to form first and second images on the retina of a person's eye; and
   movable means attached to said slit aperture plate, said lens system and said monochromatic light source for moving said slit aperture plate, said lens system and said monochromatic light source together in a fixed relationship along said first optical axis to enable the person to align the first and second images.

7. The optometer apparatus of claim 6 wherein said lens system includes:
   a converging lens disposed between said monochromatic light source and said slit aperture plate for focusing the light image from said monochromatic light source; and
   a cylinder lens positioned between said converging lens and said slit aperature plate for shaping the focused light image from said converging lens to fit within said vertical slit after passing through said third and fourth polarizing filters.

8. The optometer apparatus of claim 6 wherein said pinhole aperture plate further includes a third aperture located between said first and second horizontally positioned apertures, said optometer apparatus further including:
   an elongated hollow tube disposed in said third aperture; and
   a second monochromatic light source for internally illuminating said elongated hollow tube with light at a second wavelength to form a third image to aid the person to align said first and second images.

9. The optometer apparatus of claim 6 further including:
   a beam splitter for enabling the person to view said first and second images.

10. The optometer apparatus of claim 6 wherein:
    said positive lens is a Badal lens.

11. The optometer apparatus of claim 8 further including:
    a beam splitter for enabling the person to view said third image superposed over said first and second images.

12. A method for measuring the dark focus of accomodation of the eye of a subject, said method comprising the steps of:
    providing first and second apertures positioned on opposite sides of an optical axis for viewing by the subject's eye;

covering the first and second apertures with respective first and second orthogonally oriented polarizing filters;

providing a target;

covering first and second portions of the target with respective third and fourth polarizing filters respectively oriented parallel to the first and second polarizing filters to form an orthogonally polarized target;

projecting a monochromatic image of the orthogonally polarized target through the first and second apertures as first and second rays of light; and adjusting the positions of the first and second rays of light into vernier alignment to measure the dark focus of accomodation of the subject's eye.

13. The method of claim 12 wherein said projecting step includes the steps of:

emitting monochromatic light from a monochromatic light source;

using a first lens to focus the monochromatic light;

utilizing a second lens to shape the focused monochromatic light to pass through the orthoganally polarized target; and employing a third lens to focus the monochromatic image of the orthogonally polarized target through the first and second apertures.

14. The method of claim 13 wherein said adjusting step includes the step of:

moving in unison the monochromatic light source, the first and second lenses and the orthogonally polarized target relative relative to the third lens and first and second apertures until the first and second rays of light are in vernier alignment.

15. The method of claim 12 wherein said providing step includes the step of:

utilizing two pinhole apertures positioned on opposite sides of the optical axis of a pinhole aperture plate as the first and second apertures.

16. An optometer apparatus having an optical axis for measuring the dark focus of accommodation of the eye of a subject, said optometer apparatus comprising:

means for providing first and second apertures positioned on opposite sides of said optical axis to be viewed by the eye of said subject;

means for covering said first and second apertures with respective first and second orthogonally oriented polarizing filters;

means for providing a target;

means for covering first and second portions of said target with respective third and fourth polarizing filters respectively oriented parallel to said first and second polarizing filters to form an orthogonally polarized target;

means for projecting a monochromatic image of said orthogonally polarized target through said first and second apertures as first and second rays of light; and means for adjusting the positions of said first and second rays of light into vernier alignment to measure the dark focus of accommodation of the eye of said subject.

17. The optometer apparatus of claim 16 wherein said providing means includes:

a pinhole aperture plate containing said first and second apertures horizontally positioned on opposite sides of the first optical axis.

18. The optometer apparatus of claim 17 wherein:

said first and second apertures are Scheiner apertures.

19. The optometer apparatus of claim 16 wherein said projecting means includes:

a monochromatic light source disposed on said optical axis;

a lens system on said optical axis for focusing light from said monochromatic light source into said orthogonally polarized target; and a lens disposed on said optical axis for focusing said monochromatic image of said orthogonally polarized target through said first and second apertures.

20. The optometer apparatus of claim 16 wherein said lens system includes:

a converging lens disposed between said monochromatic light source and said orthogonally polarized target for focusing the monochromatic light from said monochromatic light source; and a cylinder lens positioned between said converging lens and said orthogonally polarized target for shaping the focused light from said converging lens to pass through said orthogonally polarized target.

* * * * *